US009034365B2

(12) United States Patent
Shalaby et al.

(10) Patent No.: US 9,034,365 B2
(45) Date of Patent: *May 19, 2015

(54) BIOSTABLE, MULTIPURPOSE, MICROBICIDAL INTRAVAGINAL DEVICES

(75) Inventors: Shalaby W. Shalaby, Anderson, SC (US); Georgios T. Hilas, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 1133 days.

This patent is subject to a terminal disclaimer.

(21) Appl. No.: 12/448,022

(22) PCT Filed: May 11, 2009

(86) PCT No.: PCT/US2009/002897
§ 371 (c)(1),
(2), (4) Date: Jun. 4, 2009

(65) Prior Publication Data
US 2010/0330138 A1   Dec. 30, 2010

Related U.S. Application Data

(60) Provisional application No. 61/128,221, filed on May 20, 2008.

(51) Int. Cl.
  *A61F 6/14*  (2006.01)
  *A61K 31/4174*  (2006.01)
  *A61K 31/42*  (2006.01)
  *A61F 6/08*  (2006.01)

(52) U.S. Cl.
  CPC ............ *A61K 31/4174* (2013.01); *A61F 6/08* (2013.01); *A61K 31/42* (2013.01)

(58) Field of Classification Search
  CPC .................................................. A61K 9/0036
  USPC ........................................................ 424/432
  See application file for complete search history.

(56) References Cited

U.S. PATENT DOCUMENTS

| 4,629,449 | A * | 12/1986 | Wong | 604/515 |
| 6,416,779 | B1 * | 7/2002 | D'Augustine et al. | 424/430 |
| 2004/0077601 | A1 * | 4/2004 | Adams et al. | 514/64 |
| 2004/0260386 | A1 * | 12/2004 | Shalaby | 623/1.15 |
| 2004/0265355 | A1 | 12/2004 | Shalaby | |
| 2005/0053639 | A1 | 3/2005 | Shalaby | |
| 2006/0195142 | A1 * | 8/2006 | Shalaby | 606/228 |
| 2008/0069850 | A1 | 3/2008 | Shalaby | |
| 2009/0291925 | A1 * | 11/2009 | Shalaby | 514/152 |

FOREIGN PATENT DOCUMENTS

WO   PCT US 05/45190   12/2005

OTHER PUBLICATIONS

U.S. Appl. No. 11/667,933, filed May 16, 2007, Shalaby.

* cited by examiner

*Primary Examiner* — Benjamin Packard
(74) *Attorney, Agent, or Firm* — McNair Law Firm, P.A.; Douglas L. Lineberry

(57) ABSTRACT

Biostable, multipurpose, microbicidal intravaginal devices in the form of rings, ringed-meshes, sponges, or diaphragms for use by women and condoms for use by male partners are provided, wherein each of the devices contains a drug effective in treating a particular vaginal infection, while further exhibiting at least one additional function selected from the group dealing with non-hormonal contraception, management of sexually transmitted diseases, viral infections, and retroviral infections as well as the treatment of cervical cancer.

12 Claims, No Drawings

BIOSTABLE, MULTIPURPOSE, MICROBICIDAL INTRAVAGINAL DEVICES

FIELD OF THE INVENTION

The present invention is directed to a family of multipurpose microbicidal devices comprising a drug for protecting women against one particular vaginal infection, yet capable of performing at least one additional function, selected from the dealing with contraception and the management of sexually transmitted diseases, viral infections, and retroviral infections, and the treatment of cervical cancer. The devices may take the form of biostable, intravaginal sponges, diaphragms, rings, and ringed-mesh constructs for use by women and condoms for use by male partners. The drug can, for instance, be an antifungal compound, such as miconazole, that is effective in treating yeast infection and exhibits spermiostatic/spermicidal, antiviral and/or antiretroviral activities.

BACKGROUND OF THE INVENTION

Intravaginal drug delivery can be utilized for topical, local, or systemic effects. Topical administration has been used to treat various bacterial or fungal infections, atrophic vaginitis, and vaginal intraepithelial neoplasia. The most relevant prior art to the instant invention was the subject of a few patent applications by one of the present inventors. The most recent application, U.S. Ser. No. 11/974,140 (filed on Oct. 11, 2007) is directed with a ring device having multicomponent drug releasing substrates loaded with at least one bioactive agent and designed to effect contraception and/or provide means to treat and/or prevent diseases caused by infectious bacteria, fungi, virus, and retroviruses, without compromising the primary function of normally occurring, useful vaginal microflora in female patients. This application was a continuation-in-part of U.S. Ser. No. 11/667,933, filed on May 16, 2007, and entitled "Intravaginal Ringed-mesh Device and Applicator Therefor." The tenets of the prior art that preceded U.S. patent application Ser. No. 11/974,140, and related disclosures which are also relevant to this invention are outlined below.

U.S. application Ser. No. 10/860,677, hereby incorporated herein by reference in its entirety, discloses a controlled drug release device comprising a partially or fully absorbable, fiber-reinforced composite ring system comprising an absorbable or non-absorbable matrix, an absorbable, reinforcing fibrous construct and an absorbable coating to provide three modes of controlling the release of bioactive agents and one mode for modulating the mechanical property of the ring in a body cavity during device functional use. For partially absorbable ring systems, the drug release is dependent initially on the diffusion rate of the drug through the matrix and the absorbable coating. As the latter degrades with time, the diffusion through the matrix prevails. Meanwhile, as the absorbable fibrous reinforcing construct undergoes degradation with time, the mechanical strength of the composite ring decreases to provide the desired mechanical strength retention profile. For a fully absorbable composite ring system, the degradation of the matrix offers an additional mode of controlling the release profile as compared with the partially absorbable counterpart. In effect, the invention of U.S. application Ser. No. 10/860,677 deals with a fiber-reinforced composite ring system for the controlled release of at least one bioactive agent comprising a biocompatible matrix reinforced with an absorbable/biodegradable fibrous construct capable of providing the mechanical properties needed for inserting and maintaining said ring in a body cavity for the desired period of time, wherein the absorbable/biodegradable reinforcing fibers are made primarily from at least one cyclic monomer such as glycolide, l-lactide, $\epsilon$-caprolactone, p-dioxanone, and trimethylene carbonate.

U.S. application Ser. No. 10/935,808 was filed on Sep. 8, 2004 as a continuation-in-part application of U.S. Ser. No. 10/860,677, described above, and dealt with a partially absorbable, fiber-reinforced composite for the controlled delivery of at least one bioactive agent. The composite included an absorbable fiber construct capable of providing time-dependent mechanical properties of a biostable elastomeric copolymeric matrix containing an absorbable microparticulate ion-exchanging polymer to modulate the release of the bioactive agent for the desired period of time at a specific biological site. In accordance with that invention (1) the absorbable reinforcing fibers were formed from at least one cyclic monomer selected from glycolide, l-lactide, $\epsilon$-caprolactone, p-dioxanone, trimethylene carbonate, and a morpholine-2,5-dione; and (2) the biostable matrix was made of a polyether urethane elastomer or a silicone elastomer, such as a copolymer polysiloxane, including dimethyl siloxane sequences, which can be one of the Silastic® family of silicone elastomers.

Obviously, application Ser. Nos. 10/860,677 and 10/935,808 and related teachings did not disclose (1) the use of a non-absorbable reinforcing construct in the composite ring; (2) a novel cross-sectional geometry of the ring and associated clinical benefits in terms of ease of placement and minimized vaginal tissue trauma; (3) use of a novel feature entailing the presence of a mesh encircled by the composite ring, wherein such mesh can be used as a spermiostatic net in a contraceptive device and/or a depot for the release of bioactive agents including antimicrobials and antivirals; and (4) a ring applicator that can be used as needed by the patient without physician intervention. This led to a series of related applications, namely U.S. provisional application No. 60/635,887, filed on Dec. 14, 2004, PCT Application No. U.S. 05/45190, filed on Dec. 14, 2005, and U.S. application Ser. No. 11/667,933, filed on May 16, 2007, hereby incorporated herein by reference in its entirety.

U.S. application Ser. No. 11/667,933 is directed in general to an intravaginal device which is a ringed, flat mesh encircled with a fiber-reinforced composite ring, the composite ring providing for the controlled delivery of at least one bioactive agent, the ring being formed of a fibrous construct contained within a compliant, elastomeric copolymeric matrix, the fibrous construct providing adequate stiffness and resilience for in-use biomechanical stability, the copolymeric matrix further containing solid excipients to modulate the pH about the ring and the concentration of the at least one bioactive agent. More specifically, this case is directed to an intravaginal device comprising a ringed, flat mesh encircled with a fiber-reinforced composite ring for the controlled delivery of at least one bioactive agent. The ring is a fibrous construct that is capable of imparting needed stiffness, resilience, and in-use biomechanical stability to the compliant elastomeric copolymeric matrix thereof containing solid excipients to modulate the pH of the aqueous eluates and concentration of the bioactive agent or agents released therein. The mesh is a biostable, non-woven, melt-blown, porous polyolefin fabric, such as those made of polyethylene or polypropylene, having an average pore diameter of less than 100 microns and preferably less than 20 microns and more preferably less than 7 microns and the encircling ring is made of a crosslinked silicone elastomeric copolymer reinforced with a circular band of high-melting multifilament yarn sized with a low-melting polymer. In a specific situation, the flat fabric mesh is made of melt-blown fabric comprising polypropylene microdenier fibers and the fiber-reinforced composite ring is a crosslinked silicone elastomer reinforced with polyethylene terephthalate multifilament band sized with poly-ε-caprolactone wherein the matrix contains ferrous gluconate or ferrous ascorbate as a spermiostatic/spermicidal agent and at least one excipient selected from the group represented by ascorbic acid, carboxyl-bearing polyglycolide, glycine, citric acid, oxalic acid, tartaric acid, and glycolic acid. Because of its composition and design, the intravaginal device is conceived as a multifaceted, biomechanically, biochemically, and pharmacologically active device for securing contraception in humans and animals. A key feature of such device and particularly the flat mesh is that the polypropylene fibers of the mesh are surface sulfonated to repel approaching negatively charged sperms. This is associated with the fact that the sperms have a negatively charged surface that will be repelled by the negatively charged sulfonate-bearing surface of the mesh. This and the limited porosity of the mesh, which can be associated with a pore diameter of less than 7 microns, will prevent the sperm diffusion through the mesh as the sperm has a head diameter of about 7 microns. Another key feature of the polyolefin or more specifically polypropylene flat mesh is that its fibers may contain an antimicrobial agent or agents such as triclosan. Obviously, these applications did not deal with certain aspects of the intravaginal ring system which include the use of surface-activated, knitted, ringed-mesh having an average pore diameter exceeding 100 micron—this is well beyond an order-of-magnitude difference from the sperm head diameter of about 7 micron and higher than the previously disclosed mesh pore diameter described as being less than 100 micron.

Collectively, the prior art discussed above dealt with (1) totally absorbable or partially absorbable intravaginal ring constructs and was silent on new intravaginal rings that are biostable as is the case for the instant invention; (2) intravaginal, non-hormonal spermiostatic/spermicidal agents, but was silent on the use of simple non-hormonal organic drugs that are not prescribed as effective contraceptive agents, which was surprisingly found to be the case in parts of the instant invention; (3) intravaginal non-hormonal contraceptive rings, which also exhibit antifungal or antibacterial activities due to the incorporation of an antifungal or antibacterial agent along with the non-hormonal spermiostatic/spermicidal agent, ferrous gluconate, but silent on the use of one agent that is antifungal or antibacterial and that is also spermiostatic, as is uniquely the case of the instant invention; and (4) intravaginal rings that have either antimicrobial or antiviral activity through the independent effect of at least two separate agents, but silent on the use of one particular agent to achieve, simultaneously, both antimicrobial and antiviral (or retroviral) activities as is the case of the instant invention. Additionally, the prior art was silent on the use of one particular drug of known efficacy for one indication and yet, it exhibits activity for two additional functions as in the case of the present invention. These facts and recent findings in our laboratory on unique properties of antifungal, antibacterial, and antineoplastic agents prompted the pursuit of the study, subject of the present invention.

SUMMARY OF THE INVENTION

The present invention is directed generally to a biostable, multipurpose, microbicidal intravaginal device comprising a drug effective in treating a particular vaginal infection, the drug selected from the group consisting of miconazole, ketoconazole, fluconazole, butoconazole, tioconazole, clotrimazole, mitomycin, clindamycin, doxycycline, leflunamide, 5-fluorouracil, paclitaxel, and mycophenolic acid, the drug further exhibiting at least one additional function selected from the group comprising the management of non-hormonal contraception, sexually transmitted diseases, viral infections, retroviral infections, and cervical cancer, wherein said device is in the form selected from the group consisting of sponges, diaphragms, condoms, rings, and ringed-mesh constructs. Meanwhile, in the case of the ringed-mesh construct, a ring matrix encircles a fibrous mesh adjoined thereto and held in the ring lumen, wherein the ring matrix is a silicone reinforced with polyethylene terephthalate yarn and the mesh is a polyethylene terephthalate fabric, and wherein the device is coated with a drug-containing, absorbable polymer, the coating preferably being a solid polyethylene glycol and an absorbable, segmented polyaxial polyester derived from at least two monomers selected from the group consisting of l-lactide, glycolide, trimethylene carbonate, ε-caprolactone, p-dioxanone, and a morpholinedione. Additionally, the drug-containing polymer coating includes a drug effective in treating bacterial infection selected from the group consisting of mitomycin, clindamycin, doxycycline, and related compounds.

A clinically important aspect of this invention deals with a biostable, multipurpose, microbicidal intravaginal device comprising a drug effective in treating a particular vaginal infection, the drug selected from the group consisting of miconazole, ketoconazole, fluconazole, butoconazole, tioconazole, clotrimazole, mitomycin, clindamycin, doxycycline, leflunamide, 5-fluorouracil, paclitaxel, and mycophenolic acid, the drug further exhibiting at least one additional function selected from the group comprising the management of non-hormonal contraception, sexually transmitted diseases, viral infections, retroviral infections, and cervical cancer, wherein the particular vaginal infection comprises a yeast infection and the at least one additional function comprises non-hormonal contraception, and wherein the at least one additional function further comprises the management of a retroviral infection comprising human immunodeficiency virus (HIV), and further wherein the drug-containing polymer coating comprises a drug effective in treating yeast infections, the drug selected from the group consisting of miconazole, ketoconazole, fluconazole, butoconazole, tioconazole, and clotrimazole with the drug-containing polymer coating contains 5 to 30 weight percent of micronazole.

A specific aspect of this invention deals with a biostable, multipurpose, microbicidal intravaginal device comprising a drug effective in treating a particular vaginal infection, the drug selected from the group consisting of miconazole, ketoconazole, fluconazole, butoconazole, tioconazole, clotrimazole, mitomycin, clindamycin, doxycycline, leflunamide, 5-fluorouracil, paclitaxel, and mycophenolic acid, the drug further exhibiting at least one additional function selected from the group comprising the management of non-hormonal contraception, sexually transmitted diseases, viral infections, retroviral infections, and cervical cancer, wherein said device is in the form selected from the group consisting of sponges, diaphragms, condoms, rings, and ringed-mesh constructs. Meanwhile, in the case of the ringed-mesh construct, it comprises a ringed-mesh construct comprising a fiber-reinforced ring matrix encircling a fibrous mesh adjoined thereto and held in the ring lumen, wherein the ring matrix comprises a blend of polyethylene glycol containing a drug and an ethylene vinyl acetate copolymer reinforced with polyethylene terephthalate yarn and the mesh comprises a polyethylene terephthalate fabric, and wherein the mesh is coated with an absorbable polymer comprising a segmented polyaxial polyester derived from at least two monomers derived from the group consisting of l-lactide, glycolide, p-dioxanone, trimethylene carbonate, ε-caprolactone, and a morpholinedione, and further, wherein the particular vaginal infection comprises a yeast infection and the at least one additional function comprises non-hormonal contraception. Additionally, the at least one additional function comprises the management of HIV, wherein both the ring matrix and mesh coating contain an antifungal drug selected from the group represented by miconazole, ketoconazole, fluconazole, butoconazole, tioconazole, and clotrimazole at a weight percentage of 2 to 6 and 0.5 to 4 percent by weight, respectively.

Another clinically important aspect of this invention deals with a biostable, multipurpose, microbicidal intravaginal device comprising a drug effective in treating a particular vaginal infection, the drug selected from the group consisting of miconazole, ketoconazole, fluconazole, butoconazole, tioconazole, clotrimazole, mitomycin, clindamycin, doxycycline, leflunamide, 5-fluorouracil, paclitaxel, and mycophenolic acid, the drug further exhibiting at least one additional function selected from the group comprising the management of non-hormonal contraception, sexually transmitted diseases, viral infections, retroviral infections, and cervical cancer wherein said device is in the form selected from the group consisting of sponges, diaphragms, condoms, rings, and ringed-mesh constructs. Meanwhile, in the case a ring, it comprises a melt blend of a drug-containing polyethylene glycol and an ethylene vinyl acetate copolymer, and the drug is an antifungal drug selected from the group consisting of miconazole, ketoconazole, fluconazole, butoconazole, tioconazole, and clotrimazole at a weight percent of 1 to 6, wherein the particular vaginal infection comprises a yeast infection and the at least one additional function comprises the management of HIV infection, and wherein the particular vaginal infection comprises a yeast infection and the at least additional function comprises the management of cervical cancer.

Another specific aspect of this invention deals with a biostable, multipurpose, microbicidal intravaginal device comprising a drug effective in treating a particular vaginal infection, the drug selected from the group consisting of miconazole, ketoconazole, fluconazole, butoconazole, tioconazole, clotrimazole, mitomycin, clindamycin, doxycycline, leflunamide, 5-fluorouracil, paclitaxel, and mycophenolic acid, the drug further exhibiting at least one additional function selected from the group comprising the management of non-hormonal contraception, sexually transmitted diseases, viral infections, retroviral infections, and cervical cancer, wherein said device is in the form selected from the group consisting of sponges, diaphragms, condoms, rings, and ringed-mesh constructs. Meanwhile, in the case of the ringed-mesh construct, it comprises a ringed-mesh construct comprising a fiber-reinforced ring matrix encircling a fibrous mesh adjoined thereto and held in the ring lumen, wherein the ring matrix comprises a blend of polyethylene glycol containing a drug and an ethylene vinyl acetate copolymer reinforced with polyethylene terephthalate yarn and the mesh comprises a polyethylene terephthalate fabric, and
wherein the mesh is coated with an absorbable polymer comprising a segmented polyaxial polyester derived from at least two monomers derived from the group consisting of l-lactide, glycolide, p-dioxanone, trimethylene carbonate, ε-caprolactone, and a morpholinedione, and further wherein the particular vaginal infection comprises a bacterial infection and the at least one additional function deals comprises non-hormonal contraception and the management of HIV. Additionally, both the ring matrix and mesh coating contain an antibacterial drug selected from the group consisting of mitomycin, clindamycin, doxycycline, and related compounds at a weight percentage of 2 to 6 and 0.5 to 4 percent by weight, respectively.

A special aspect of this inventions deals with a biostable, multipurpose, microbicidal intravaginal device comprising an antineoplastic drug capable of exhibiting at least one additional function from the group comprising non-hormonal contraception and management of sexually transmitted diseases, viral infections, retroviral infections, and cervical cancer, wherein the antineoplastic drug is selected from the group consisting of 5-fluorouracil, paclitaxel, and mycophenolic acid.

Another special aspect of this invention deals with a biostable, multipurpose, microbicidal intravaginal device comprising an immunosuppressant drug, comprising leflunamide, the drug exhibiting at least one additional function selected from the group comprising non-hormonal contraception and management of sexually transmitted diseases, viral infections, retroviral infections, and cervical cancer.

DETAILED DESCRIPTION OF PREFERRED EMBODIMENTS

The present invention addresses several new aspects of intravaginal controlled drug delivery focusing on uniquely multipurpose microbicides using traditional and new forms of recently disclosed ring devices. These new aspects entail (1) the use of a new family of multipurpose microbicidal devices comprising a drug for protecting women against one particular vaginal infection, such as a yeast infection, yet are capable of performing at least one additional function selected from those dealing with non-hormonal, achievable contraception, management of sexually transmitted diseases, viral and antiviral infections, and treatment of cervical cancer, as part of biostable intravaginal sponges, diaphragms, rings, ringed-mesh constructs for application by women and condoms by male partners; (2) the use of uniquely multipurpose organic compounds, such as the well-established miconazole and similar antifungal drugs, for displaying spermiostatic/spermicidal activities, thus exhibiting non-hormonal achievable contraception; (3) the use of uniquely multipurpose microbicidal drugs with established antifungal or antibacterial activities also capable of exhibiting not only spermiostatic/spermicidal activities, but also antiviral and/or retroviral activities relevant to the management of HIV and cervical cancer; and (4) biostable ringed-mesh devices designed for the controlled delivery of the selected multipurpose bioactive agents and also capable of providing barrier properties toward sperms and infected biological fluids during coition. Additionally, this invention deals with special methods of incorporating the multipurpose microbicidal agents in the different intravaginal devices and condoms. These methods entail (1) dissolving the drug in the hydrophilic (e.g., solid polyethylene glycol) component of the ring, made by melt-blending the drug-loaded polymer of an olefinic polymer (e.g., an ethylene vinyl acetate copolymer); (2) incorporating the drug in an absorbable polymer and using the resulting drug-loaded polymer for coating a silicone ring or ringed-mesh comprising a silicone ring encircling a polyester mesh (e.g., polyethylene terephthalate mesh); (3) using the drug-loaded polymer from item 2 to precoat the mesh of the ringed-mesh comprising a polyethylene terephthalate mesh and drug-coated mesh similar to the one in item 1; (4) using a flexible polyurethane microporous sponge with continuous cellular structure, which is precoated with drug-loaded absorbable polymer—alternatively, a drug solution is used to pre-swell and dry to allow the drug to diffuse and reside at the uppermost layer of the external and internal areas of the polyurethane cellular structure; (5) using a flexible polyurethane-based diaphragm pre-swelled with a solution of an absorbable or non-absorbable flexible polymer and drug followed by drying to allow the drug to diffuse and reside at the uppermost layer of the diaphragm surface—alternatively, the diaphragm is precoated with a drug-loaded, semi-solid or viscous liquid polymer, such as polyethylene glycol or block copolymers with polypropylene glycol; and (6) using a condom comprising a flexible polyurethane precoated with a drug-loaded semi-solid or viscous lubricant.

Further illustrations of the present invention are provided by the following examples:

Example 1

Preparation of a Drug-Loaded Polymeric Coating Solution

To prepare a drug-loaded polymeric coating solution the following steps were pursued. An aliquot of 0.700 grams miconazole was dissolved in a 20 mL solvent mixture comprised of a 4:1 dichloromethane:methanol. To this solution 0.415 g solid polyethylene glycol (PEG) 4600 and 1.630 g of a low molecular polyester were added and dissolved. The low molecular polyester was a triaxial copolymer made by the copolymerization of the following monomers: L-lactide, ε-caprolactone, trimethylene carbonate (TMC), and glycolide using a protocol similar to that described in U.S. Pat. No. 6,794,485, incorporated herein by reference in its entirety. The resultant polymer exhibited a molecular weight of about 150 kDa and a melting temperature of about 104° C.

Example 2

Preparation of a Typical Ringed-Mesh Having a Silicone Ring Matrix

To prepare a typical ringed mesh having a silicone ring matrix the following steps were pursued. An aliquot of 13 g of a two part biomedical-grade silicone was mixed together and injected into a ring mold preloaded with a non-absorbable scaffold affixed to a non-absorbable woven mesh. The scaffold and mesh were constructed from polyethylene terephthalate multifilament yarn. Polytetramethylene succinate was used as the sizing agent for the scaffold and as the binding agent for scaffold/mesh attachment. Once injected, the mold was then placed in an 80° C. oven for 4 hours to cure.

Example 3

Preparation of a Coated Ringed-Mesh Similar to that of Example 2 with a Miconazole-Loaded Polymeric System as in Example 1

To coat a ringed-mesh similar to that noted in Example 2 with a miconazole loaded polymeric system, as in Example 1, the following steps were pursued. Ringed mesh was dipped into the coating solution allowing coverage of the total ring for 5 seconds. The ringed-mesh was then removed from the coating solution and placed on release paper to dry under a fume hood for 1 hour. The coated ringed-mesh was then dried at room temperature under reduced pressure for 24 hours.

Using the aforementioned process, the resultant coated ring gained 168 mg which comprised 100 mg low molecular weight triaxial polyester, 25 mg PEG 4600, and 43 mg miconazole.

Example 4

Yeast Inhibition by the Miconazole-Loaded Ringed-Mesh of Example 3

To study the inhibition of *C. albicans* (target microbe), ¼ of the ring from Example 3 was incubated in Yeast Mold (YM) Broth that had been inoculated with *C. albicans*. Testing was conducted at 37° C. in the presence of 5% $CO_2$. After incubation (18-22 hrs), optical densities were read on the spectrophotometer at a wavelength of 600 nm and fresh inoculated broth was added to the ring. Percent inhibition due to the ringed-mesh was determined by comparing the optical density of ring broth to the control tube's optical density. Yeast inhibition was observed over a 6-day period and pertinent data are summarized in Table 1.

TABLE I

Percent Inhibition of *C. albicans* by Microbicidal Ringed-mesh Device

| Incubation Time (in days) | Percent Inhibition |
|---|---|
| 0.8 | 66.5 |
| 1.5 | 75.9 |
| 2.4 | 70.6 |
| 3.2 | 72.6 |
| 4.0 | 50.9 |
| 4.8 | 42.2 |
| 5.6 | 13.7 |

Example 5

Preparation of a Drug-Loaded Coated Mesh

To prepare a drug-loaded coated mesh with miconazole the following steps were pursued. The scaffold/mesh construct was prepared as in Example 2. The coating solution was prepared as in Example 1. The mesh construct was then dipped into the coating solution for 5 seconds and placed under a fume hood to dry. Final solvent removal was conducted at room temperature under reduced pressure.

Example 6

Preparation of a Non-Silicone Based Miconazole-Loaded Ringed-Mesh

To prepare a non-silicone-based ringed-mesh loaded with miconazole the following steps are pursued. Three grams of PEG 4600 are placed in a beaker in a 130° C. oven. Once the PEG melts, 600 mg miconazole are added and then mixed thoroughly. To this, 12 grams of ethylene vinyl acetate copolymer (EVA) are added, mixed thoroughly, and placed back in the 130° C. oven. This mixing step is repeated 4 times (5 minutes between mixings) before transferring to an aluminum syringe that is preheated to 130° C. The molten mixture is then injected into an aluminum ring mold that has been pre-loaded with drug containing mesh/scaffold construct from Example 5.

Example 7

Preparation of a Non-Silicone-Based Miconazole-Loaded Ring

To prepare a non-silicone-based ring loaded with miconazole the steps shown in Example 6 are performed without using the scaffold/mesh component.

Using the aforementioned process, the resultant ring weighs 4.101 g, comprising 3.155 g EVA, 789 mg PEG 4600, and 158 mg miconazole.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A biostable, multipurpose, microbicidal intravaginal device comprising a drug effective in treating a yeast or bacterial vaginal infection, the drug selected from the group consisting of miconazole, ketoconazole, fluconazole, butoconazole, tioconazole, clotrimazole, mitomycin, clindamycin, doxycycline, leflunamide, 5-fluorouracil, paclitaxel, and mycophenolic acid, the device being in the form of a ringed-mesh construct comprising a fiber-reinforced ring matrix encircling a fibrous mesh positioned within the ring matrix and adjoined thereto and held in the ring lumen;
   wherein the fibrous mesh extends across and substantially covers the ring lumen; and
   wherein the ring matrix comprises a silicone reinforced with polyethylene terephthalate yarn and the mesh comprises a polyethylene terephthalate fabric.

2. A biostable, multipurpose, microbicidal intravaginal device as in claim 1, wherein the device is coated with a drug-containing polymer, the polymer comprising a blend of a solid polyethylene glycol and an absorbable, segmented polyaxial polyester derived from at least two monomers selected from the group consisting of l-lactide, glycolide, trimethylene carbonate, $\epsilon$-caprolactone, p-dioxanone, and a morpholinedione.

3. A biostable, multipurpose, microbicidal intravaginal device as in claim 2 wherein the drug-containing polymer coating comprises a drug selected from the group consisting of miconazole, ketoconazole, fluconazole, butoconazole, tioconazole, and clotrimazole.

4. A biostable, multipurpose, microbicidal intravaginal device as in claim 3 wherein the drug-containing polymer coating contains 5 to 30 weight percent of miconazole.

5. A biostable, multipurpose, microbicidal intravaginal device as in claim 1 wherein the ring matrix comprises a blend of drug-containing polyethylene glycol and an ethylene vinyl acetate copolymer reinforced with polyethylene terephthalate yarn and the mesh comprises a polyethylene terephthalate fabric.

6. A biostable, multipurpose, microbicidal intravaginal device as in claim 5 wherein the mesh is coated with a drug-containing polymer comprising a segmented polyaxial polyester derived from at least two monomers derived from the group consisting of l-lactide, glycolide, p-dioxanone, trimethylene carbonate, $\epsilon$-caprolactone, and a morpholinedione.

7. A biostable, multipurpose, microbicidal intravaginal device as in claim 6 wherein both the ring matrix and mesh coating contain an antifungal drug selected from the group represented by miconazole, ketoconazole, fluconazole, butoconazole, tioconazole, and clotrimazole at a weight percentage of 2 to 6 and 0.5 to 4 percent by weight, respectively.

8. A biostable, multipurpose, microbicidal intravaginal device as in claim 1 wherein the ring comprises a melt blend of a drug-containing polyethylene glycol and an ethylene vinyl acetate copolymer, and wherein the drug is an antifungal drug selected from the group consisting of miconazole, ketoconazole, fluconazole, butoconazole, tioconazole, and clotrimazole at a weight percent of 1 to 6.

9. A biostable, multipurpose, microbicidal intravaginal device as in claim 2 wherein the drug-containing polymer coating comprises a drug effective in treating bacterial infection selected from the group consisting of mitomycin, clindamycin, doxycycline, and related compounds.

10. A biostable, multipurpose, microbicidal intravaginal device as in claim 6 wherein both the ring matrix and mesh coating contain an antibacterial drug selected from the group consisting of mitomycin, clindamycin, doxycycline, and related compounds at a weight percentage of 2 to 6 and 0.5 to 4 percent by weight, respectively.

11. A biostable, multipurpose, microbicidal intravaginal device as in claim 6 wherein the drug-containing segmented polyaxial polyester is a triaxial polyester made from glycolide, 1-lactide, epsilon-caprolactone, and trimethylene carbonate.

12. A biostable, multipurpose, microbicidal intravaginal device as in claim 1 wherein the drug is miconazole.

* * * * *